(12) United States Patent
Pan (10) Patent No.: US 6,272,201 B1
(45) Date of Patent: Aug. 7, 2001

(54) METHODS AND APPARATUS FOR EFFICIENT DATA ACQUISITION IN CT SCANNERS

(75) Inventor: Tin-Su Pan, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/400,015

(22) Filed: Sep. 21, 1999

(51) Int. Cl.$^7$ .................................................. A61B 6/03
(52) U.S. Cl. ............................ 378/19; 378/4; 378/901
(58) Field of Search .................... 378/19, 4, 901

(56) References Cited

U.S. PATENT DOCUMENTS

| | | | |
|---|---|---|---|
| 5,680,427 | 10/1997 | Dobbs et al. | 378/19 |
| 5,828,273 | * 10/1998 | Harrison | 333/127 |
| 5,953,388 | * 9/1999 | Walnut et al. | 378/901 |
| 5,974,109 | * 10/1999 | Hsieh | 378/901 |
| 6,047,040 | * 4/2000 | Hu et al. | 378/901 |
| 6,137,857 | * 10/2000 | Hoffman et al. | 378/19 |

FOREIGN PATENT DOCUMENTS

| | | |
|---|---|---|
| 19502574 | 8/1996 | (DE) . |
| 19835873 | 5/1999 | (DE) . |
| 2074415 | 10/1981 | (GB) . |
| 11206751 | 8/1999 | (JP) . |

* cited by examiner

*Primary Examiner*—Drew Dunn
(74) *Attorney, Agent, or Firm*—Armstrong Teasdale LLP; Christian G. Cabou (57) ABSTRACT

In one aspect, the present invention is a method for imaging an object utilizing a multi-slice CT imaging system having an x-ray source, a detector array, and a data acquisition system coupled to the detector array, the data acquisition system having a number of data acquisition input channels less than a total number of detector cells in the detector array. The method includes steps of: positioning the object between the x-ray source and the detector array; projecting an x-ray beam towards the object; and selectively reconfiguring a coupling of selected detector cells to the data acquisition input channels to increase a number of image slices received by the data acquisition system.

20 Claims, 9 Drawing Sheets

METHODS AND APPARATUS FOR EFFICIENT DATA ACQUISITION IN CT SCANNERS

BACKGROUND OF THE INVENTION

This invention relates generally to methods and apparatus for efficiently utilizing data acquisition hardware in CT scanners, and more particularly to methods and apparatus for adjusting data acquisition hardware in CT scanners to efficiently accommodate objects of different sizes.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

At least one known CT imaging system is a multiple-slice CT scanner that scans over a large area of an imaged object in a short period of time. In comparison with single-slice CT scanners, multiple-slice CT scanners have an x-ray source projecting a more widely collimated x-ray beam and multiple rows of detectors. This scanner is thus able to reconstruct thinner slices of images (i.e., the scanner has finer spatial resolution in the table translation, or z-direction) when scanning a patient, and does not require x-ray tube cooling.

To acquire multiple rows of data from the detector of the multiple-slice CT scanner, however, requires an increased amount of data acquisition hardware. For example, if there are m rows of n detector cells, there must be mxn data acquisition channels. By comparison, a single-slice CT scanner has only n detector cells and only n data acquisition channels.

One multiple-slice CT scanner having 16 rows of detector channels is constructed in such a manner that 16 rows of 1.25 mm slices of data are made available for image reconstruction. However, to utilize all of these rows requires both a large communication bandwidth in sending data through a slip ring to the host computer, and a large amount of data acquisition hardware to acquire all of the channels.

In one known CT scanning system, only 4 rows of data are acquired simultaneously. Therefore, this system provides four different slice thicknesses, and only four slices at one time, specifically, 4×1.25 mm (central four detector rows), 4×2.50 mm (central 8 rows, adjacent rows combined), 4×3.75 mm (central 12 rows, joined in groups of three), and 4×5.00 mm (all 16 rows, combined in groups of four).

The limitation to only four simultaneously acquired slices in this system is primarily a result of data acquisition hardware limitations, even though it would be possible, for example, to provide as many as 16 slices 1.25 mm thick with the detector hardware.

The limitations of this known CT scanning system are such that large objects, up to 50 cm in diameter, such as a thorax of a patient, are nevertheless scanned rather efficiently. However, for smaller objects, such as a patient's head, utilization of the scanning channels is rather inefficient. A head typically resides in a scan field of view of less than 25 cm. The percentage of detector cells or data acquisition channels contributing to the smaller field of view is only about 56.8%, which means that about 43.2% of the data acquisition channels are idle or providing data not contributing to image reconstruction when the scanner is imaging a patient's head. (The percentages are not exactly 50% because the scanner's detector channels are not concentric with the scanner's rotating gantry.)

It would therefore be desirable to provide methods and apparatus to efficiently utilize the idle or inefficiently used data acquisition channels when imaging smaller objects such as a patient's head.

BRIEF SUMMARY OF THE INVENTION

There is therefore provided, in one embodiment, a method for imaging an object utilizing a multi-slice CT imaging system having an x-ray source, a detector array, and a data acquisition system coupled to the detector array, the data acquisition system having a number of data acquisition input channels less than a total number of detector cells in the detector array. The method includes steps of: positioning the object between the x-ray source and the detector array; projecting an x-ray beam towards the object; and selectively reconfiguring a coupling of selected detector cells to the data acquisition input channels to increase a number of image slices received by the data acquisition system.

It will be appreciated that the selective reconfiguration of detector cells to data acquisition system input channels advantageously enables idle or inefficiently used imaging channels to receive data from additional detector slices that would otherwise not be processed by an imaging channel. As a result, a greater number of image slices of small objects may be obtained and processed into images than would otherwise be possible for a given limited number of data acquisition system input channels.

DETAILED DESCRIPTION OF THE INVENTION

Figure 1:
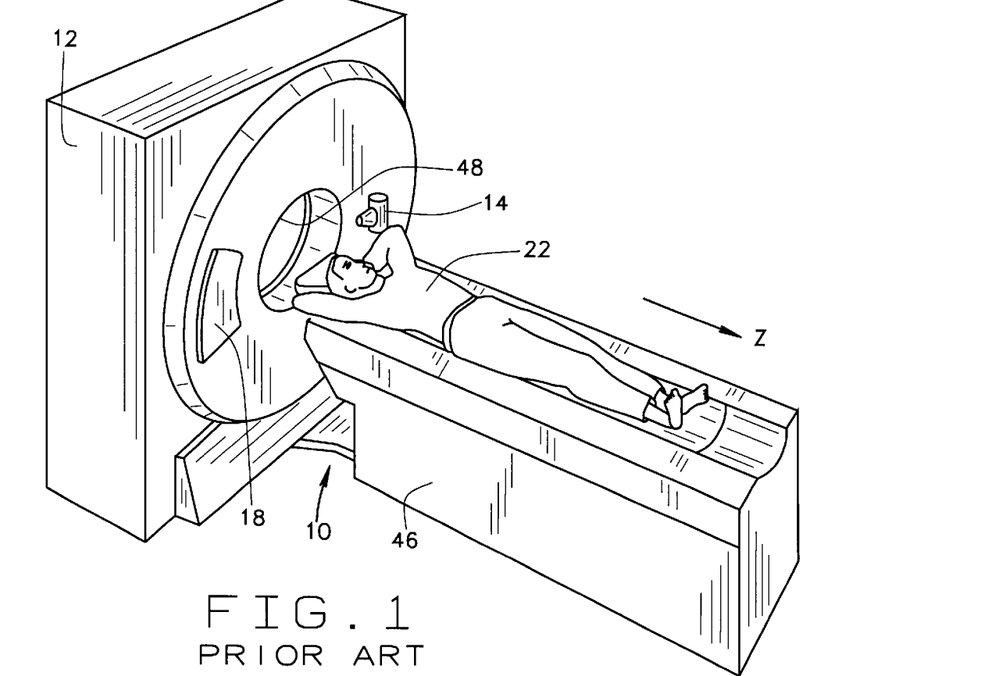
FIG. 1 is a pictorial view of a conventional CT imaging system.
Figure 2:
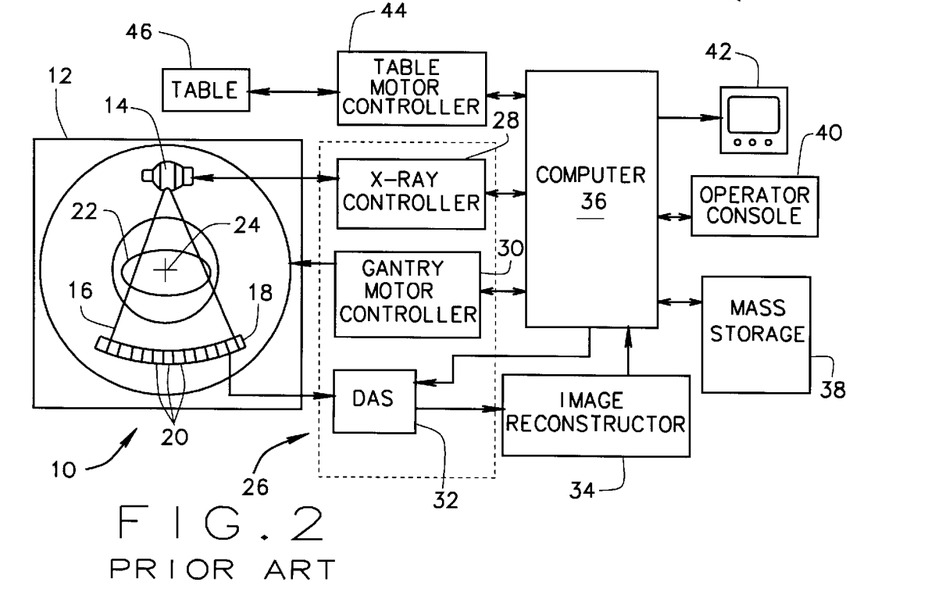
FIG. 2 is a block schematic diagram of the conventional system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 that together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 that stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 in gantry 12. Particularly, table 46 moves portions of patient 22 through gantry opening 48.

Figure 3:
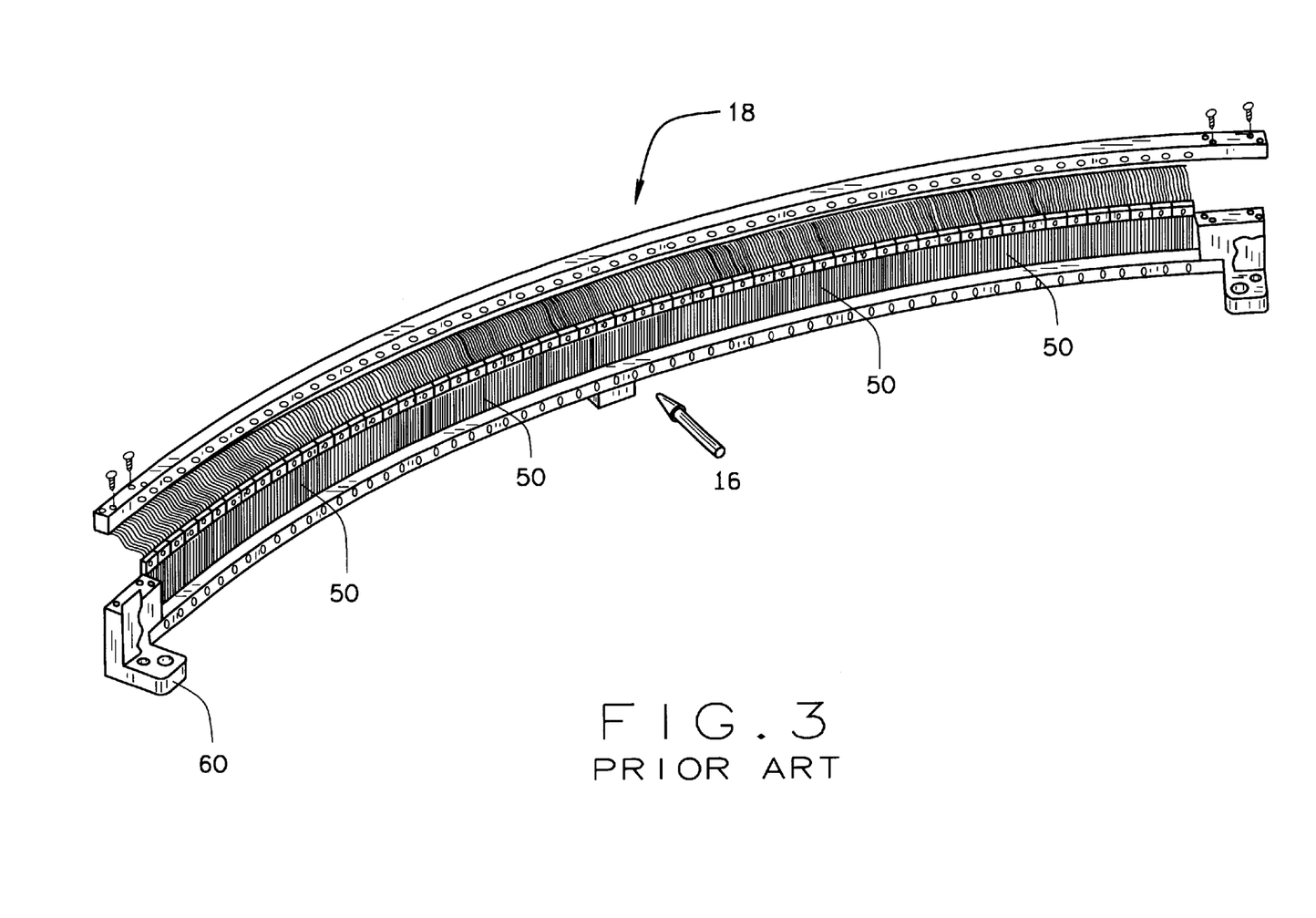
FIG. 3 is a perspective view of a conventional CT system detector array.
Figure 4:
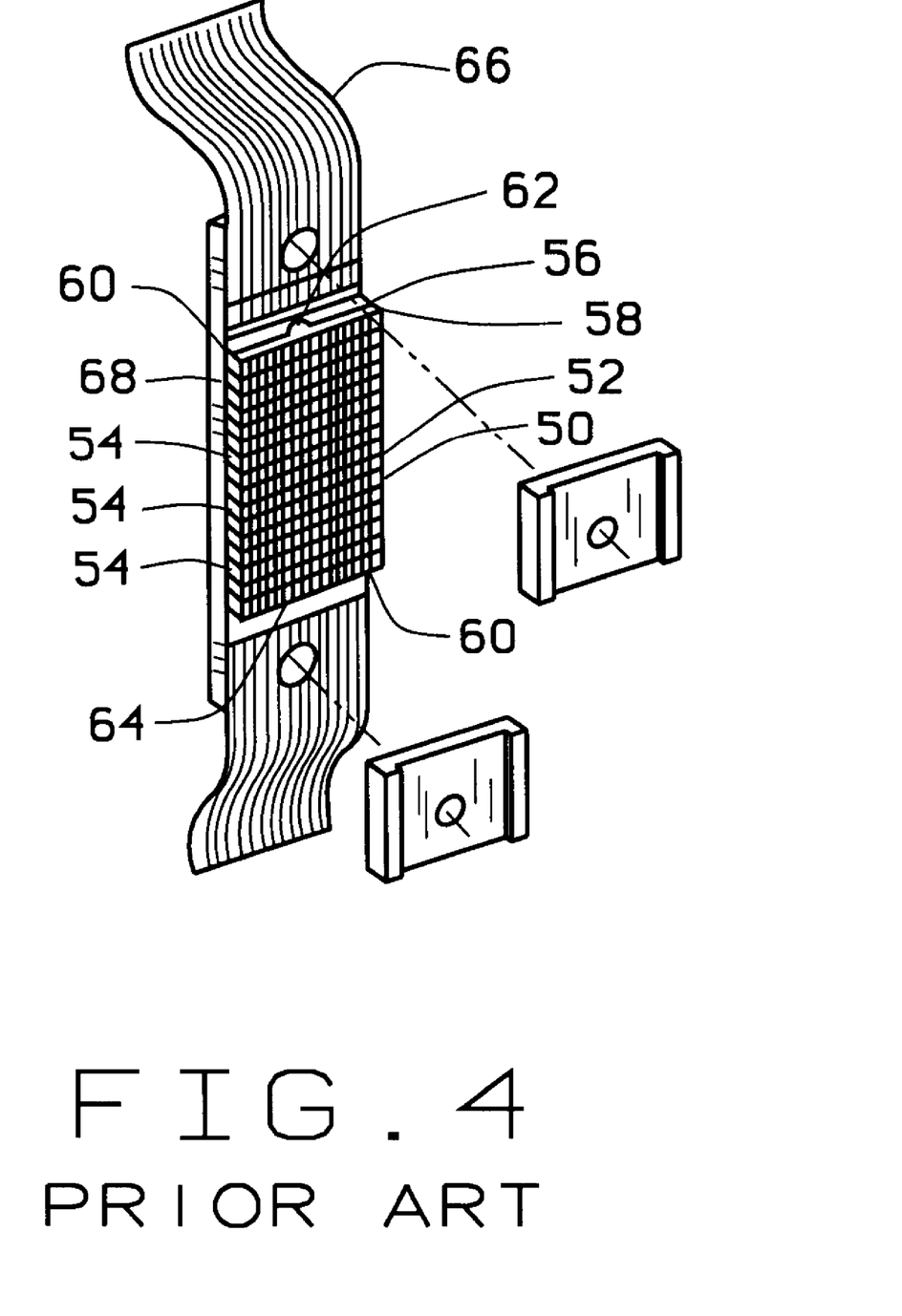
FIG. 4 is a perspective view of a conventional detector module shown in FIG. 3.

As shown in FIGS. 3 and 4, detector array 18 includes a plurality of detector modules 20. Each detector module 20 includes a high-density semiconductor array 50 and a multidimensional scintillator array 52 positioned above and adjacent to semiconductor array 50. A collimator (not shown) is positioned above and adjacent scintillator array 52 to collimate x-ray beams 16 before such beams impinge upon scintillator array 52. Particularly, semiconductor array 50 includes a plurality of photodiodes 54, a switch apparatus 56, and a detector 58. Photodiodes 54 are either individual photodiodes or a multidimensional diode array. Scintillator array 52, as known in the art, is positioned over and adjacent photodiodes 54. Photodiodes 54 are optically coupled to scintillator array 52 and have electrical output lines 60 for transmitting signals representative of the light output by scintillator array 52. Each photodiode 54 produces a separate low level analog output signal that is a measurement of beam attenuation for a specific scintillator of scintillator array 52. Photodiode output lines 60 are, for example, physically located on one side of module 20 or on a plurality of sides of module 20. As shown in FIG. 4, photodiode outputs 60 are located at opposing sides of the photodiode array.

In one embodiment, detector array 18 includes fifty-seven detector modules 20. Each detector module 20 includes a semiconductor array 50 and scintillator array 52, each having an array size of 16×16. As a result, array 18 has 16 rows and 912 columns (16×57 modules) allowing up to N=16 simultaneous slices of data to be collected along a z-axis with each rotation of gantry 12, where the z-axis is an axis of rotation of the gantry.

Switch apparatus 56 is a multidimensional semiconductor switch array of similar size as semiconductor array 50. Switch apparatus 56 is coupled between semiconductor array 50 and DAS 32. Semiconductor device 56, in one embodiment, includes two semiconductor switches 62 and 64. Switches 62 and 64 each include a plurality of field effect transistors (FETs) (not shown) arranged as a multidimensional array. Each FET includes an input line electrically connected to one of the respective photodiode output lines 60, an output line, and a control line (not shown). FET output and control lines are electrically connected to DAS 32 via an electrical cable 66. Particularly, about one-half of photodiode output lines 60 are electrically connected to each FET input line of switch 62 with the other one-half of photodiode output lines 60 electrically connected to FET input lines of switch 64.

Decoder 58 controls the operation of switch apparatus 56 to enable, disable, or combine photodiode outputs 68 in accordance with a desired number of slices and slice resolutions for each slice. Decoder 58, in one embodiment, is a decoder chip or an FET controller as known in the art. Decoder 58 includes a plurality of output and control lines coupled to switch apparatus 56 and DAS 32. Particularly, the decoder outputs are electrically coupled to the switch apparatus control lines to enable switch apparatus 56 to transmit the proper data from the switch apparatus inputs to the switch apparatus outputs. Utilizing decoder 58, specific FETs within switch apparatus 56 are enabled, disabled, or combined so that specific photodiode outputs 68 are electrically connected to CT system DAS 32. In one embodiment defined as a 16 slice mode, decoder 58 enables switch apparatus 56 so that all rows of semiconductor array 50 are connected to DAS 32, resulting in 16 simultaneous slices of data being electrically connected to DAS 32. Of course, other slice combinations are also possible.

Figure 5:
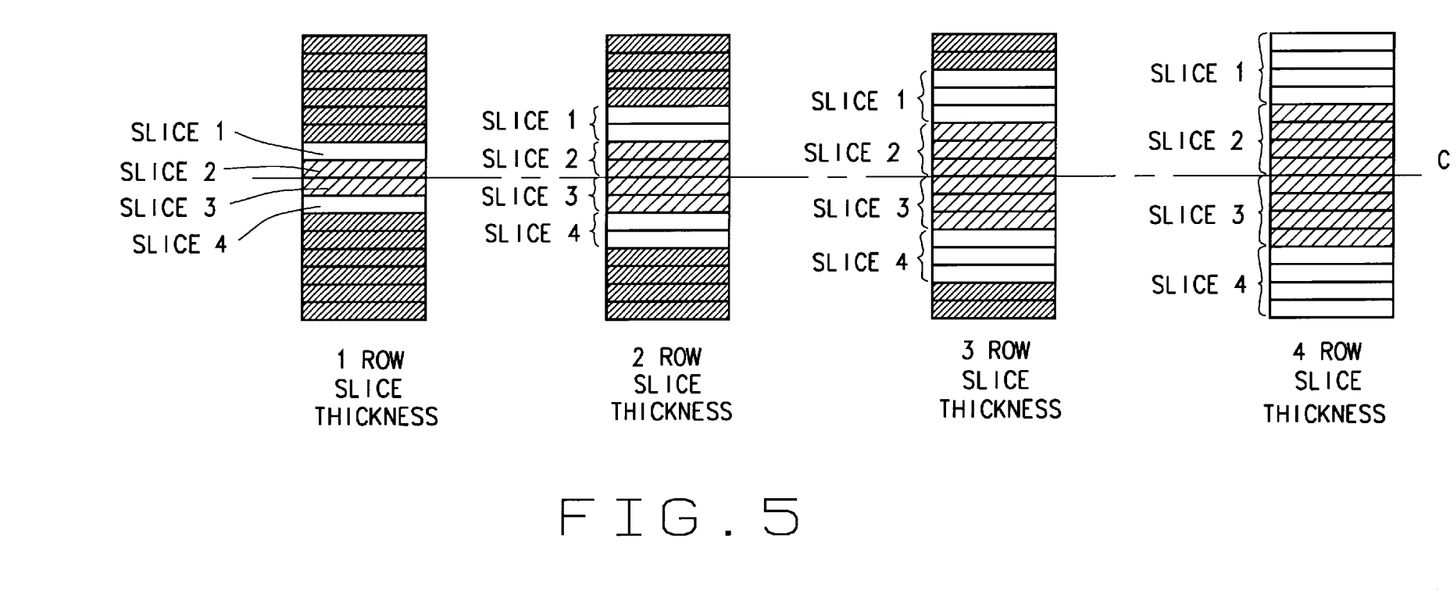
FIG. 5 is illustrative of various configurations of the detector module of FIG. 4 in a four-slice mode.

For example, decoder 58 selects from other multiple slice modes, including one, two, and four slice modes. As shown in FIG. 5, by transmitting the appropriate decoder control lines, switch apparatus 56 can be configured in the four slice mode so that data is collected from four slices of one or more rows of photodiode array 50. Depending upon the specific configuration of switch apparatus 56 as defined by decoder control lines, various combinations of photodiode outputs 68 can be enabled, disabled, or combined so that the slice thickness may consist of 1, 2, 3, or 4 rows of photodiode array elements. Additional examples include a single slice mode including one slice with slices ranging from 1.25 mm thick to 20 mm thick; and a two-slice mode including two slices with slices ranging from 1.25 mm thick to 10 mm thick. Additional modes other than those described herein are also possible.

Figure 6:
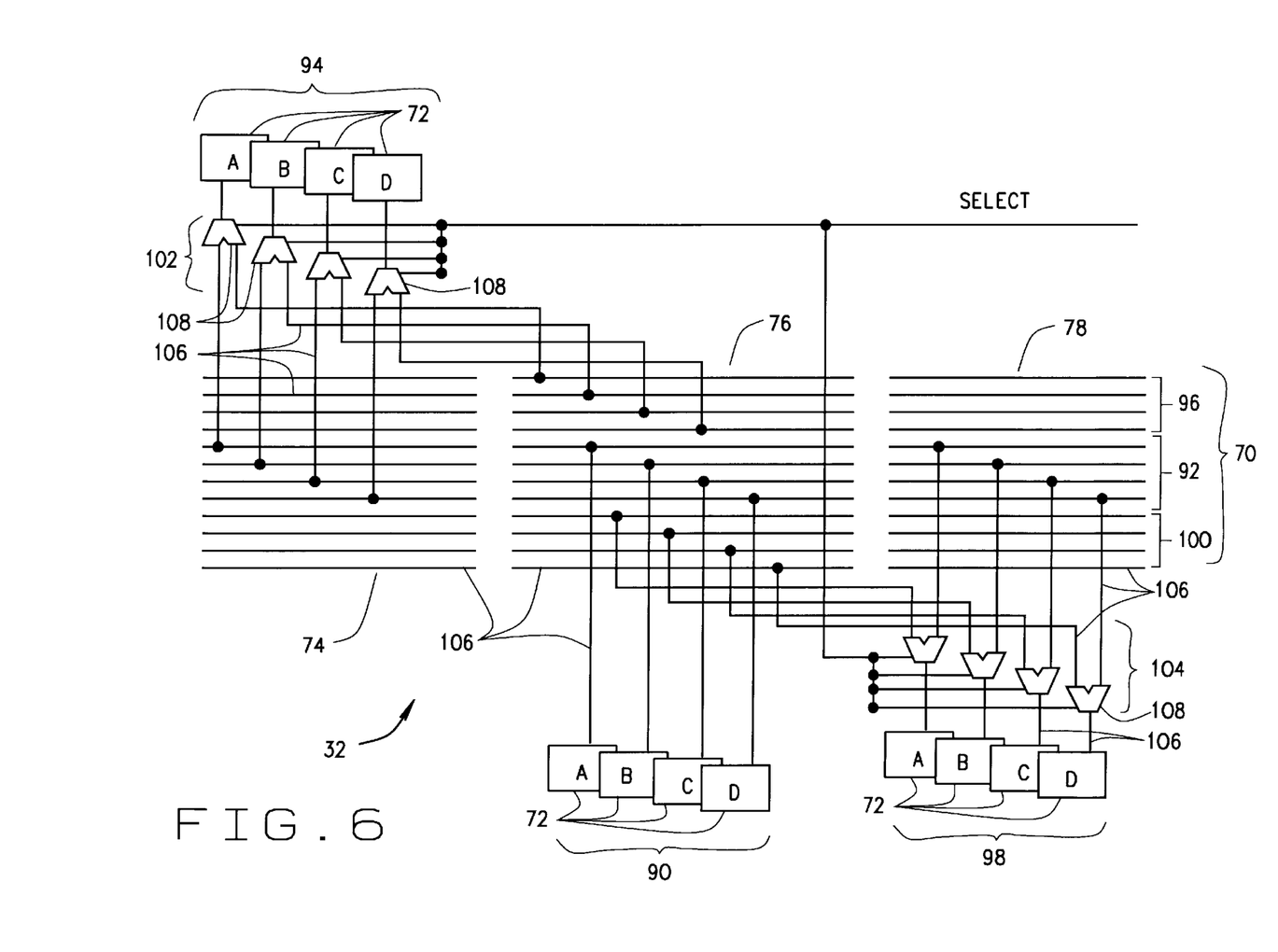
FIG. 6 is a drawing of a block diagram of a simplified embodiment of a backplane and data acquisition system useful for explaining embodiments of the present invention.

Analog current signals from detector array 18 are connected to DAS 32 input channels via cables 66 connected to DAS 32 at a DAS backplane 70, shown in the DAS 32 and backplane 70 block diagram of FIG. 6. In one embodiment, DAS converter boards or input processors 72, each processing 64 input channels, are plugged into DAS backplane 70. Backplane 70 provides a redistribution of the detector cells to appropriate converter board 72 input channels. A serial bus (not shown) interconnects corresponding (A, B, C, D) DAS converter boards 72, coupling them to imaging reconstructor 34.

In one embodiment, each of the 64 channels of DAS converter board 72 processes analog data from a selected detector element or cell 20 and converts the data into a digital form that is utilized by image reconstructor 34. (The invention can be practiced with DAS converter boards 72 configured to process a number of channels different from 64.) Converter boards 72 thus provide fewer input channels than the number of detector cells 20 in array 18. Adding a capability to process image data for more than four slices in this embodiment would normally require more serial data streams as well as additional DAS converter boards 72.

FIG. 6 shows only three twelve-slice backplane 70 sections 74, 76, and 78 that are each electrically coupled to three azimuthal sets of twelve rows of sixty-four detector cells 20. For purposes of explaining the invention, it will suffice to consider a simplified example based on FIG. 6. Extensions to larger, more practical systems will be evident to one skilled in the art upon achieving a full understanding of the simplified example of FIG. 6. Such larger systems include those having a greater number of backplane 70 sections, a greater number of azimuthal sets and rows of detector cells 20, and a greater number of DAS converter boards 72, for example.

Figure 7:
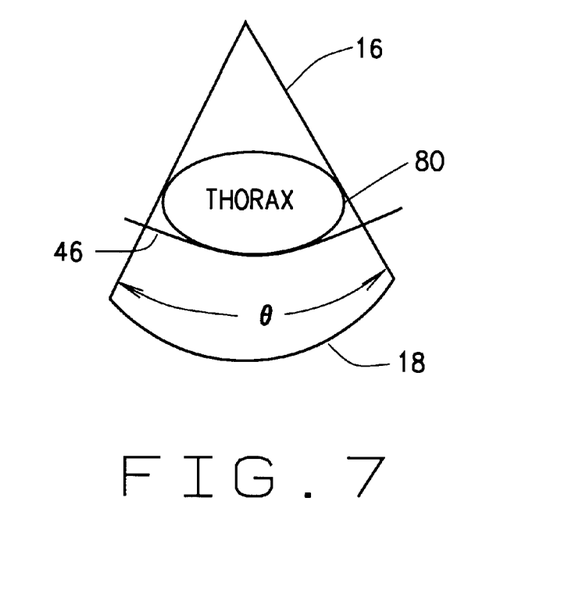
FIG. 7 is a representation of the detector array of the imaging system of FIG. 1 collecting image data representative of a patient's thorax.
Figure 8:
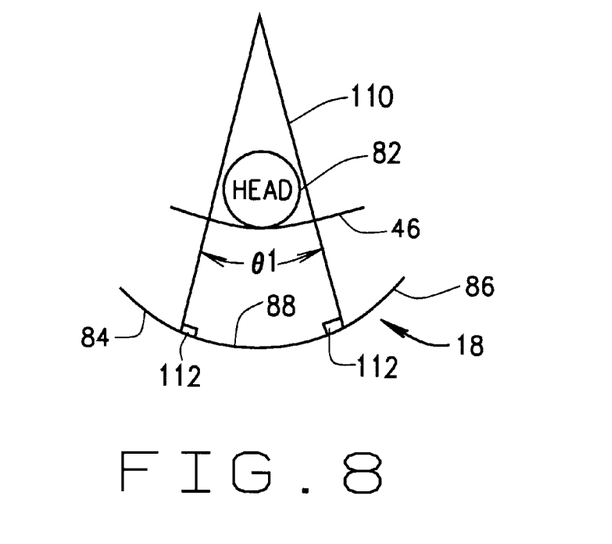
FIG. 8 is a representation of the detector array of the imaging system of FIG. 1 collecting image data representative of a patient's head.

In one embodiment of the present invention, 16 slice imaging capability at a reduced fan angle is provided without utilizing additional converter boards 72 by multiplexing inputs of some of converter boards 72. As shown in FIG. 7, when a large object such as a thorax 80 of patient 22 is scanned, a full extent of beam 16 is used. As a result, full use of fan angle θ of detector 18 is utilized. However, the full fan angle θ is not required in all situations, as shown in FIG. 8. When head 82 of patient 22 is scanned, an azimuthal extent θ1<θ of detector 18 suffices for data acquisition. Unused data channels of converter boards 72 that are normally receiving data from detector elements at peripheral azimuthal detector regions 84 and 86 have their inputs switched to other detector elements 20 to provide additional slice coverage of data within central azimuthal detector region 88. This redirection can be used whenever azimuthal extent θ1 alone is adequate for imaging an object.

As illustrated in the simplified example of FIG. 6, a plurality of DAS converter boards 72 having multiplexed input channels are plugged into DAS backplane 70. In this simplified example, backplane 70 sections 74, 76, 78 are electrically coupled to azimuthal regions 84, 88, and 86, respectively, of detector 18. A DAS converter board set 90 electrically coupled to central backplane section 76 is permanently configured in this exemplary embodiment to receive data from detector cells 20 in a group of four central rows 92 of a central region 88 of detector 18. DAS converter board set 94 is also electrically coupled to a group of four central rows 92 of detector 18, but at backplane section 74, corresponding to peripheral section 84 of detector 18. DAS converter board set 94 is also electrically coupled to an additional set of rows 96 in central backplane section 76, which corresponds to a central region 88 of detector 18. Similarly, DAS converter board set 98 is electrically coupled to a group of four central rows 92 of detector 18 at backplane section 78 and to an additional set of rows 100 in central backplane section 76. For a first state of a SELECT line, multplexer groups 102 and 104 are configured so that data from peripheral backplane sections 74 and 78 are input to DAS converter board sets 94 and 98, respectively. For a second, different state of the SELECT line, additional row sets 96 and 100 of central backplane section 76 are input to DAS converter board sets 94 and 98, respectively. Each row of backplane 70 in this embodiment comprises 64 data channels. Therefore, a physical realization of data lines such as 106 in FIG. 6 can vary according to design choice. In different embodiments, data lines such as data lines 106 in FIG. 6 are single conductors, multiple parallel data lines, serial busses, or combinations thereof. Each multiplexer 108 shown in FIG. 6 is realized accordingly as one or more multiplexers or as a functionally equivalent circuit.

Figure 9:
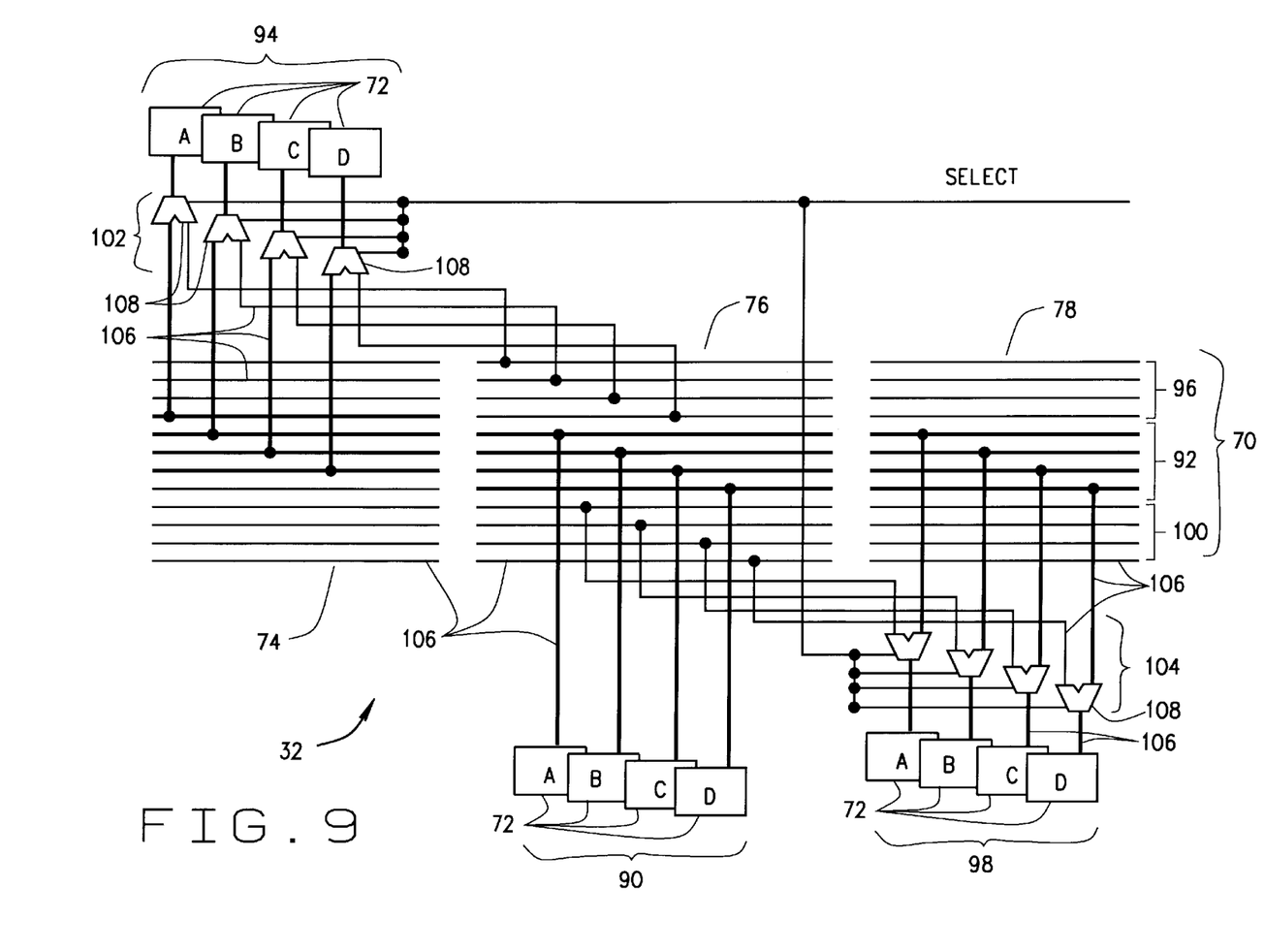
FIG. 9 is a drawing of the block diagram of the embodiment of FIG. 6 showing an input configuration of data acquisition system converter boards in a first selected state.

Referring to FIG. 9, when image data is required from three azimuthal regions 84, 86, and 88, as when a thorax 80 is imaged, the SELECT line is in a first state. This first state is represented in FIG. 9 by a thinly drawn SELECT line. In this first state, multiplexer groups 102 and 104 pass data from peripheral azimuthal regions 84 and 86 to DAS board groups 94 and 98 via backplane sections 74 and 78, respectively. Data lines 106 that are selected for input to DAS boards 72 are indicated by heavier lines. In this selected state, 4 rows of data of an entire azimuthal extent θ of detector 18 in the simplified embodiment illustrated in FIG. 9 are available for processing into image slices. In this simplified embodiment, four rows is a maximum limit to a number of complete rows that can be processed by the number of DAS converter boards 70 in imaging system 10.

Figure 10:
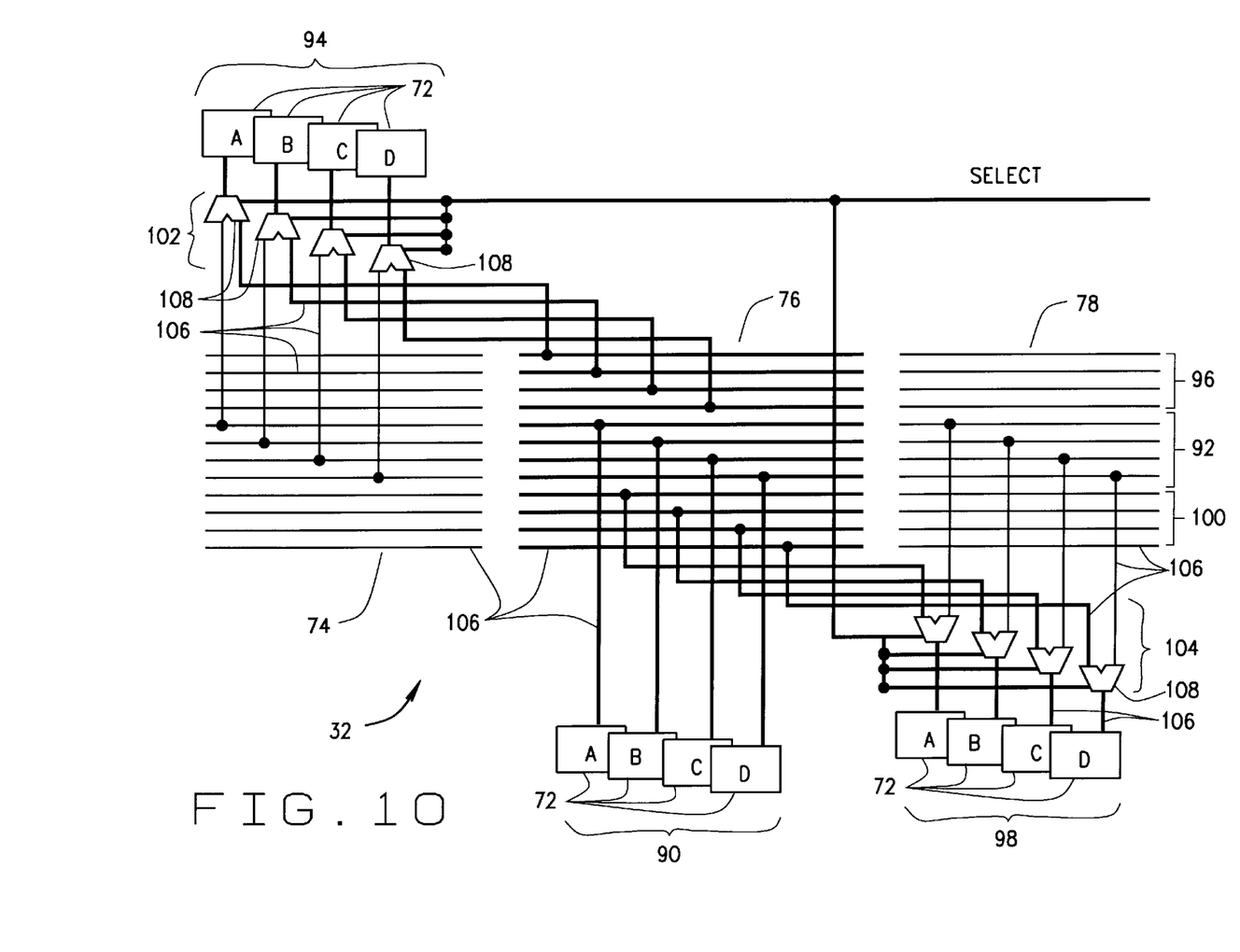
FIG. 10 is a drawing of the block diagram of the embodiment of FIG. 6 showing an input configuration of data acquisition system converter boards in a second selected state.

Referring to FIG. 10, head 82 is not in a path between x-ray source 14 and azimuthal detector regions 84 and 86. Thus, when a head 82 or another small object is imaged, data from peripheral azimuthal regions 84, 86 of detector array 18 is not needed. In one embodiment of the present invention, effective use of DAS converter board groups 94 and 98 is provided by a second state of the SELECT line, represented in FIG. 10 by a heavily drawn SELECT line. Inputs to DAS converter board groups 94 and 98 are provided in this second state by additional row sets 96 and 100, respectively, of central azimuthal region 88 of detector 18 via backplane section 76. Data lines 106 that are selected for input to DAS boards 72 are indicated by heavier lines. In this selected state, image data is available for 12 image slices in a region θ1 of sufficient azimuthal extent to provide useful images of head 82 of patient 22, or another small object. Without this second selection state being available, data for only four image slices would be available. Also, four rows of detector 18 in peripheral azimuthal detector regions 84 and 86 would contribute no useful imaging data.

A state of SELECT line is, in one embodiment, controlled by a switch on operator console 40. A state of the SELECT line is supplied not only to multiplexers 108 in DAS 32, but also to image reconstructor 34 and computer 36. Thus, image reconstructor 34 and computer 36 are provided with necessary multiplexer state information so that output data from DAS converter boards 72 is correctly interpreted, assembled into images, and displayed.

Extension of the simplified example of FIGS. 6, 9, and 10 to other, more practical embodiments should be readily apparent. For example, in one embodiment having 57 DAS converter board sets similar to sets 90, 94 and 98, more than two peripheral board sets 94 and 98 have switchable, selectable inputs. A 16 slice detector 18 is provided as is a 16 row backplane 70. Sufficient DAS converter boards 72 are provided for processing four image slices at a time having full azimuthal extent θ. By switching inputs for converter boards 72 of a plurality of peripheral board groups similarly to groups 94 and 98 of FIGS. 6, 9, and 10, an alternative selectable configuration is provided that optimizes coverage of smaller objects. An alternative configuration selected by multiplexers 108 is optimized in accordance with several factors. These factors include a number of available DAS converter boards 72, a number of rows in backplane 70, and an azimuthal extent of an attenuation shadow cast by a head 82 or other small object on image detector array 18. In general, it is not required that all DAS converter boards 72 in a group be coupled to multiplexers or that all channels of any particular DAS board 72 be coupled to multiplexers. It is also not required that a set of multiplexers 108 coupled to DAS converter boards 72 in a group all be coupled to the same backplane 70 sections. Rather, an alternative input configuration for DAS converter board 72 channels selected by multiplexers 108 can be selected to optimize imaging efficiency.

The embodiment illustrated in FIGS. 6, 9, and 10 shows multiplexers 108 external to DAS boards 72. However, in another embodiment, multiplexers 108 are provided on DAS boards 72. In another embodiment, multiplexing is provided on a detector side of backplane 70 rather than on a DAS side.

In one embodiment of the present invention having a detector 18 capable of N=16 slices of 1.25 mm minimum width, four DAS converter boards 72 are provided for each backplane 70 section. A total of 43.2% of detector board 72 channels are reassignable by switching. In this embodiment, up to a 75% increase in coverage of small objects can be provided with additional slices as tabulated in the following table. Listings under "43.2% Idle" are numbers of slices available when no input channel reassignment is provided. Listings under "100% Channel Use" are the numbers of slices available when an alternative input configuration is selected. Multiplexing in this embodiment is used to rearrange input channels to provide more detector imaging slices in a centralized azimuthal region 88 of detector 18. (In this embodiment, azimuthal region 88 is coupled to more than one backplane 70 section. Similarly, peripheral regions 84 and 86 are coupled to more than one backplane 70 section.)

| Slice Width | 43.2% Idle | 100% Channel Use | Coverage Increase |
| --- | --- | --- | --- |
| 1.25 mm | P = 4 slices | Q = 7 slices | 75% |
| 2.50 mm | P = 4 slices | Q = 7 slices | 75% |
| 3.75 mm | P = 4 slices | Q = 5 slices* | 25% |
| 5.00 nm | P = 4 slices | Q = 4 slices* | 0% |

In the preceding table, (*) indicates that the capacity of data acquisition exceeds the capacity of the detector in this acquisition mode, i.e., there are no detector channels available. The coverage improvements given above are maximum coverage improvements. In other embodiments, between 25% and 50% of DAS input channels are reconfigured by multiplexing.

It will be observed that there are two approaches to pre-patient collimating x-ray beam 110 when imaging head 82 of patient 22. A first approach is to use a wide beam 16 in imaging an object of about 50 cm diameter, such as thorax 80 in FIG. 7. Wide beam 16 is selected to cover fan width θ of detector 18. However, a wide beam is not necessary for imaging objects of approximately 25 cm diameter such as a head 82 in FIG. 8. The use of wide beams 16 in such instances produce a potential to incur more scattered x-ray photons, thus increasing a radiation dose of patient 22. Instead, to image objects of approximately 25 cm in diameter, a narrow beam 110 is selected to cover a portion of detector array 18 having fan angle θ1. Use of narrower beam 110 results in patient 22 being potentially exposed to a lower radiation dose. Reference channels 112 used for normalization of the reconstructed image, and which are usually at extremities of x-ray beam 16 are assigned closer to detector channels 88 in a 25 cm scan field of view provided by narrow beam 110. However, table 46 blocks these reference channels because of the narrower beam. Data from the reference channels is corrected by recording the x-ray tube 14 mA current signal in a header of the scan beam data and renormalizing the reference channel data in accordance with the mA current signal. This renormalization may be performed by image reconstructor 34 or by computer 36.

Figure 11:
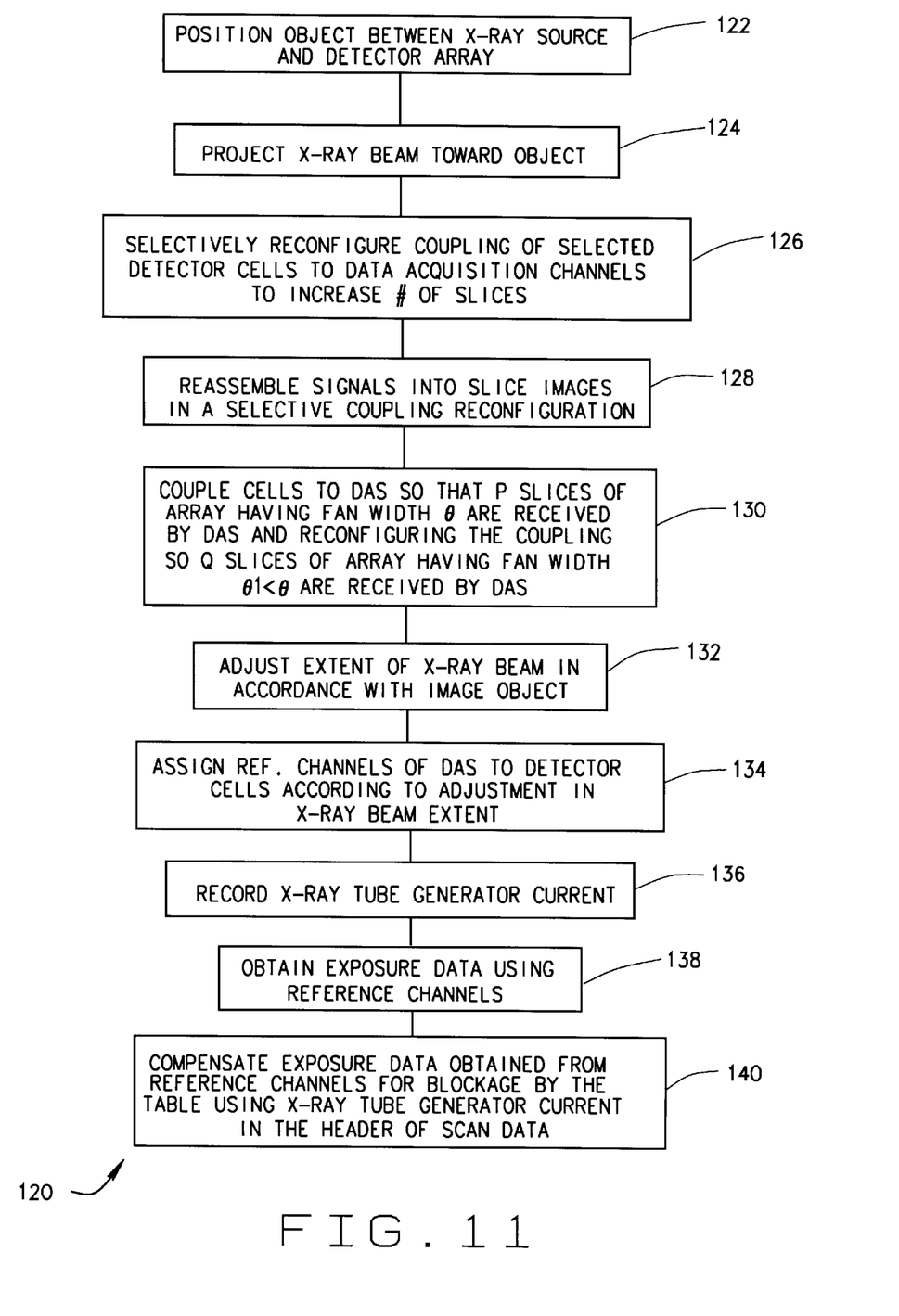
FIG. 11 is a flowchart illustrating steps for imaging an object.

FIG. 11 is a flowchart 120 illustrating steps for imaging an object utilizing a CT scanner 10 (shown in FIG. 1) having the features disclosed herein. In one embodiment, a patient is positioned 122 between x-ray source 14 (shown in FIGS. 1 and 2) and cells of detector array 18 (shown in FIGS. 1 and 2), such as by placing the object, or patient 22 (shown in FIGS. 1 and 2) on table 46 (shown in FIGS. 1 and 2). An x-ray beam 16 (shown in FIG. 2) is projected 124 towards the patient. A selective reconfiguration of a coupling of selected detector cells to data acquisition channels is performed 126. For example, a switch on operator console 40 (shown in FIG. 2) is set to select a state of a group of multiplexers. The reconfiguration 128 is such that data channels of DAS 32 (shown in FIG. 2) that would otherwise not be useful in imaging a small portion of patient 22 (for example, the head 82 (shown in FIG. 8) of patient 22) are used to process additional image slices. This reconfiguration is possible because it is sufficient to process data from detector array 18 having reduced azimuthal extent when small objects are imaged. To accommodate the selective redirection, data from DAS 32 is reassembled by image reconstructor 34 (shown in FIG. 2) to reconstruct the image slices. In one embodiment, signals are reassembled 128 from DAS 32 into slice images with selective coupling reconfiguration.

As described above, and in a further embodiment, detector cells are coupled 130 to DAS 32 so that a number of slices P<N of detector array 18 having fan width θ are received by DAS 32. Also coupling 130 of detector cells 20 (shown in FIG. 2) to DAS 32 is done so that a number of slices Q>P of detector array 18 having fan width θ1<θ are received by DAS 32. In one embodiment described above, θ1 has a diameter of 25 cm. and θ has a diameter of 50 cm. In such an embodiment, between 25% and 50% of detector channels to detector cells 20 are reconfigured through coupling, 43.2% in one exemplary embodiment. Other embodiments exist, wherein width of the image slices is 1.25 mm, or alternatively 2.5 mm. Further and in another exemplary embodiment, detector array 18 is capable of 16 slices of 1.25 mm minimum width, but seven slices of detector data is 100% usage of the available channels and four slices are idle. In another alternative embodiment, where imaging system 10 has a table 46, and x-ray source 14 is adjustable to an extent of the x-ray beam 16, the x-ray beam is adjusted 132 according to the size of an object to be imaged, and reference channels of DAS 32 are assigned 134 to detector cells, according to x-ray beam adjustment. Continuing, x-ray tube generator current is recorded 136 in a header of scan data, thereby obtaining 138 exposure data utilizing the reference channels and compensating 140 the exposure data obtained from the reference channels for blockage by the table utilizing the x-ray tube generator current in the header of the scan data.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Moreover, embodiments of the invention may be used with systems performing either axial or helical scans. Accordingly, the spirit and scope of the invention are to be limited only by the terms of the appended claims.

What is claimed is:

1. A method for imaging an object utilizing a multislice CT imaging system having an x-ray source, a detector array, and a data acquisition system coupled to the detector array, the data acquisition system having a number of data acquisition input channels less than a total number of detector cells in the detector array;

said method comprising the steps of:
positioning the object between the x-ray source and the detector array;
projecting an x-ray beam towards the object; and
selectively reconfiguring a coupling of selected detector cells to the data acquisition input channels to increase a number of image slices received by the data acquisition system.

2. A method in accordance with claim 1 further comprising the step of reassembling signals from the data acquisition system into slice images in accordance with said selective coupling reconfiguration.

3. A method in accordance with claim 2 further comprising the step of coupling the detector cells to the data acquisition system so that a number of slices P<N of said detector array having fan width $\theta$ are received by said data acquisition system;
and wherein selectively reconfiguring a coupling of detector cells the data acquisition input channels comprises the step of selectively reconfiguring a coupling of detector cells to the data acquisition system so that a number of slices Q>P of the detector array having fan width $\theta1<\theta$ are received by the data acquisition system.

4. A method in accordance with claim 3 further comprising selecting said fan width $\theta$ to provide imaging of an object having a diameter of 50 cm, and selecting said fan beam width $\theta1$ to provide imaging of an object having a diameter of 25 cm.

5. A method in accordance with claim 3 wherein selectively reconfiguring a coupling of detector cells to the data acquisition system so that a number of slices Q>P of the detector array having fan width $\theta1<\theta$ are received by the data acquisition system comprises the step of reconfiguring a coupling of between 25% and 50% of said detector channels to said detector cells.

6. A method in accordance with claim 3 wherein selectively reconfiguring a coupling of detector cells to the data acquisition system so that a number of slices Q>P of the detector array having fan width $\theta1<\theta$ are received by the data acquisition system comprises the step of reconfiguring a coupling of 43.2% of said detector channels to said detector cells.

7. A method in accordance with claim 3 wherein N=16, P=4, and Q=7.

8. A method in accordance with claim 7 wherein a width of the image slices is 1.25 mm.

9. A method in accordance with claim 7 wherein a width of the image slices is 2.5 mm.

10. A method in accordance with claim 3 wherein the imaging system has a table, and the x-ray source is adjustable to adjust an extent of the x-ray beam, and further comprising the steps of:
adjusting an extent of the x-ray beam in accordance with a size of the object to be imaged;
assigning reference channels of said data acquisition system to detector cells in accordance with the adjustment of the extent of the x-ray beam;
recording an x-ray tube generator current in a header of scan data;
obtaining exposure data utilizing the reference channels; and
compensating the exposure data obtained from the reference channels for blockage by the table utilizing the x-ray tube generator current in the header of the scan data.

11. A multi-slice imaging system comprising:
a multi-slice detector array having a fan angle width $\theta$ comprising multiple rows extending along a z-axis and configured to collect a maximum of N slices of image data;
an x-ray source having an x-ray beam directed towards said detector array;
a data acquisition system coupled to said detector array, said data acquisition system having input processors together having a number of data acquisition input channels fewer in number than a total number of detector cells in said detector array; and
a multiplexer array coupled between said detector and said input processors and configured to selectively reconfigure a coupling of selected ones of said detector cells to said data acquisition input channels.

12. A system in accordance with claim 11 further comprising an image reconstructor coupled to said data acquisition system and configured to reassemble said image signals into slice images in accordance with said selective coupling reconfiguration.

13. A system in accordance with claim 12 wherein said multiplexer array is configured to selectively reconfigure a coupling to selected detector cells so that, in a first coupling configuration, a number of slices P<N of said detector array having fan width $\theta$ are converted by said data acquisition system, and in a second state of said multiplexer array, a number of slices Q>P of said detector array having fan width $\theta_1<\theta$ are converted by said data acquisition system.

14. A system in accordance with claim 13 wherein said fan width $\theta$ is selected to provide imaging of an object having a diameter of 50 cm, and said fan beam width $\theta_1$ is selected to provide imaging of an object having a diameter of 25 cm.

15. A system in accordance with claim 13 wherein said multiplexer in said second state reconfigures a coupling of between 25% and 50% of said detector channels to said detector cells.

16. A system in accordance with claim 15 wherein said multiplexer in said second state reconfigures a coupling of 43.2% of said detector channels to said detector cells.

17. A system in accordance with claim 13 wherein N=16, P=4, and Q=7.

18. A system in accordance with claim 17 wherein a width of said slices is 1.25 mm.

19. A system in accordance with claim 17 wherein a width of said slices is 2.5 mm.

20. A system in accordance with claim 13 and further comprising a table, and said x-ray source comprising a variable pre-patient collimated x-ray source to adjust an extent of said x-ray beam, said system configured to assign reference channels of said data acquisition system to detector cells in accordance with a selected pre-patient collimation of said x-ray source, to record an x-ray tube generator current in a header of scan data, and to compensate exposure data from said reference channels using said x-ray tube generator current in said header of said scan data when said reference channels are blocked by said table.

* * * * *